(12) United States Patent
Minagawa et al.

(10) Patent No.: US 11,226,330 B2
(45) Date of Patent: *Jan. 18, 2022

(54) METHOD FOR CAPTURING SPECIFIC CELLS

(71) Applicants: SUMITOMO RUBBER INDUSTRIES, LTD., Kobe (JP); YAMAGATA UNIVERSITY, Yamagata (JP); OSAKA UNIVERSITY, Suita (JP)

(72) Inventors: Yasuhisa Minagawa, Kobe (JP); Masaru Tanaka, Yonezawa (JP); Takashi Hoshiba, Yonezawa (JP); Haruka Emura, Yonezawa (JP); Masaki Mori, Suita (JP); Hirofumi Yamamoto, Suita (JP); Naotsugu Haraguchi, Suita (JP)

(73) Assignees: SUMITOMO RUBBER INDUSTRIES, LTD., Kobe (JP); YAMAGATA UNIVERSITY, Yamagata (JP); OSAKA UNIVERSITY, Suita (JP)

(*) Notice: Subject to any disclaimer, the term of this patent is extended or adjusted under 35 U.S.C. 154(b) by 94 days.

This patent is subject to a terminal disclaimer.

(21) Appl. No.: 16/249,527

(22) Filed: Jan. 16, 2019

(65) Prior Publication Data

US 2019/0250151 A1 Aug. 15, 2019

(30) Foreign Application Priority Data

Feb. 14, 2018 (JP) ............................. JP2018-024092

(51) Int. Cl.
*G01N 33/50* (2006.01)
*B01D 21/26* (2006.01)
*G01N 33/574* (2006.01)
*G01N 33/543* (2006.01)

(52) U.S. Cl.
CPC ........ *G01N 33/5091* (2013.01); *B01D 21/262* (2013.01); *G01N 33/543* (2013.01); *G01N 33/574* (2013.01)

(58) Field of Classification Search
CPC .......... G01N 33/5091; G01N 33/574; G01N 33/543; G01N 33/5005; B01D 21/262; C12N 5/0693; C12N 2509/00
See application file for complete search history.

(56) References Cited

U.S. PATENT DOCUMENTS

| | | | |
|---|---|---|---|
| 9,372,136 B2 * | 6/2016 | Kanbara ............... | G01N 1/405 |
| 2006/0008807 A1 | 1/2006 | O'Hara et al. | |
| 2012/0077246 A1 | 3/2012 | Hong et al. | |
| 2012/0156698 A1 | 6/2012 | Jendoubi | |
| 2013/0059288 A1 | 3/2013 | Dankbar et al. | |
| 2014/0158604 A1 * | 6/2014 | Chammas ............. | A61M 1/3616 210/256 |
| 2014/0299539 A1 * | 10/2014 | Takai ..................... | B01D 39/10 210/506 |
| 2015/0285786 A1 | 10/2015 | Hahn et al. | |
| 2016/0069861 A1 | 3/2016 | Santore et al. | |
| 2016/0136552 A1 | 5/2016 | Nakanishi et al. | |
| 2016/0291019 A1 | 10/2016 | Yoon et al. | |
| 2017/0113218 A1 * | 4/2017 | Chen ................... | B01L 3/502753 |
| 2017/0225166 A1 | 8/2017 | Toner et al. | |
| 2018/0088105 A1 * | 3/2018 | Minagawa ............ | G01N 33/5005 |
| 2019/0233555 A1 * | 8/2019 | Minagawa ............ | C08J 7/0423 |

FOREIGN PATENT DOCUMENTS

| | | |
|---|---|---|
| EP | 0225703 A2 | 6/1987 |
| EP | 2720039 A1 | 4/2014 |
| EP | 3244208 A1 | 11/2017 |
| EP | 3301443 A1 | 4/2018 |
| EP | 3301444 A1 | 4/2018 |
| EP | 3527985 A1 | 8/2019 |
| EP | 3527986 A1 | 8/2019 |
| JP | 2-10160 A | 1/1990 |
| JP | 2004-522937 A | 7/2004 |
| JP | 2005-82538 A | 3/2005 |
| JP | 2005-523981 A | 8/2005 |
| JP | 2012-522217 A | 9/2012 |
| JP | 2013-174616 A | 9/2013 |
| JP | 2014-105159 A | 6/2014 |
| JP | 2015-224332 A | 12/2015 |
| JP | 2016-131561 A | 7/2016 |
| JP | 2016-158019 A | 9/2016 |
| JP | 2017-523431 A | 8/2017 |
| WO | WO 02/20825 A1 | 3/2002 |

(Continued)

OTHER PUBLICATIONS

Klockner and Buchs. Advances in shaking technologies. Trends in Biotechnology 2012 vol. 30(6). pp. 307-314.*

He et al., "Quantitation of Circulating Tumor Cells in Blood Samples from Ovarian and Prostate Cancer Patients Using Tumor-Specific Fluorescent Ligands", International Journal of Cancer, vol. 123, 2008, pp. 1968-1973.

Hoshiba et al., "Adhesion-Based Simple Capture and Recovery of Circulating Tumor Cells Using a Blood-Compatible and Thermo-Responsive Polymer-Coated Substrate," RSC Advances, vol. 6, 2016 (Published on Sep. 13, 2016), pp. 89103-89112.

(Continued)

*Primary Examiner* — Blaine Lankford
(74) *Attorney, Agent, or Firm* — Birch, Stewart, Kolasch & Birch, LLP

(57) ABSTRACT

The present invention provides a method for capturing specific cells (e.g. many types of cancer cells, including cancer cells not expressing EpCAM) and a method for analysis of specific cells involving the method. Included is a method for capturing specific cells present in blood or biological fluid, the method including: subjecting sampled blood or biological fluid to enrichment; and capturing specific cells therefrom onto a hydrophilic polymer layer in a flow field.

10 Claims, 1 Drawing Sheet

(56) References Cited

FOREIGN PATENT DOCUMENTS

| WO | WO 03/093367 A1 | 11/2003 |
|---|---|---|
| WO | WO 2006/108087 A2 | 10/2006 |
| WO | WO 2007/092028 A2 | 8/2007 |
| WO | WO 2010/111388 A2 | 9/2010 |
| WO | WO 2011/017094 A2 | 2/2011 |
| WO | WO 2012/108087 A1 | 8/2012 |
| WO | WO 2015/012315 A1 | 1/2015 |
| WO | WO 2016/103002 A1 | 6/2016 |
| WO | WO 2016/115537 A2 | 7/2016 |

OTHER PUBLICATIONS

Khoo et al., "Liquid Biopsy and Therapeutic Response: Circulating Tumor Cell Cultures for Evaluation of Anticancer Treatment," Sci. Adv., vol. 2, e1600274, Jul. 13, 2016, pp. 1-15 (total 16 pages).

Vona et al., "Isolation by Size of Epithelial Tumor Cells, A New Method for the Immunomorphological and Molecular Characterization of Circulating Tumor Cells," American Journal of Pathology, vol. 156, No. 1, Jan. 2000, pp. 57-63.

Williams, "Circulating Tumor Cells," PNAS, vol. 110, No. 13, Mar. 26, 2013, pp. 4861.

Yao et al., "Functional Analysis of Single Cells Identifies a Rare Subset of Circulating Tumor Cells with Malignant Traits," Integr Biol (Camb), vol. 6, No. 4, Apr. 2014, pp. 368-398 (total 20 pages).

\* cited by examiner (a)
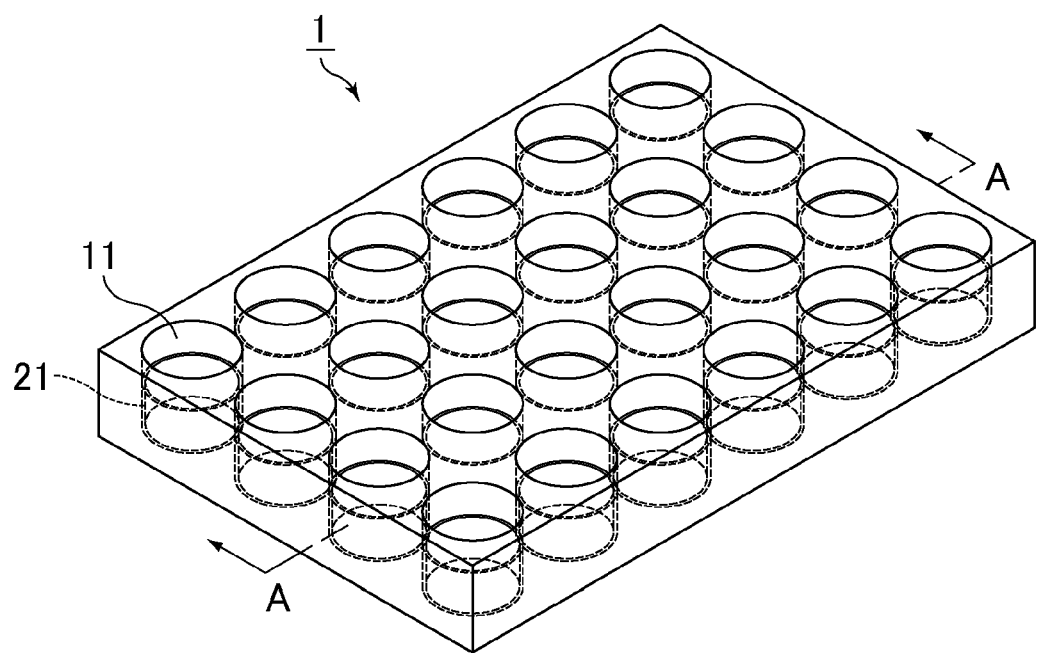
(b)
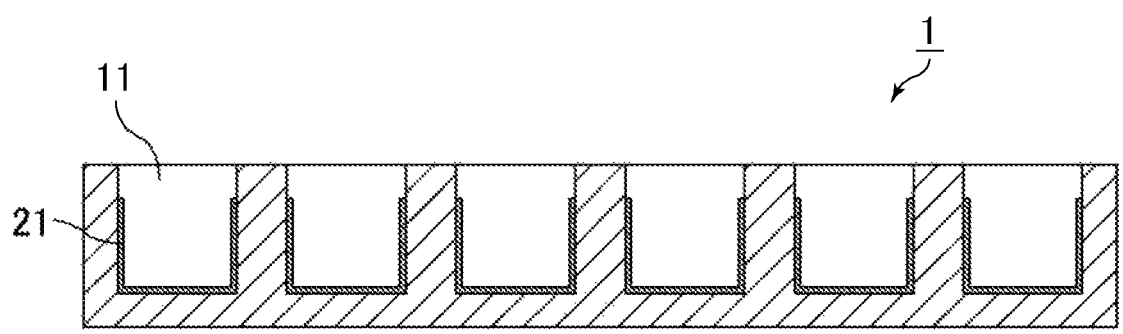
A-A cross-sectional view

METHOD FOR CAPTURING SPECIFIC CELLS

TECHNICAL FIELD

The present invention relates to a method for capturing specific cells (e.g. cancer cells present in blood or biological fluid) from blood or biological fluid, and a method for analysis of specific cells.

BACKGROUND ART

When cancer cells are formed, they are known to appear in due course in blood or biological fluid. Such cancer cells appearing in blood are called "circulating tumor cells (CTCs)". Thus, it can be expected that the circulating tumor cells may be analyzed, e.g. to evaluate the cancer-treating effect, predict prognosis life expectancy, predict the effect of anticancer drugs before administration, or examine treatment methods based on genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which involves an antigen-antibody reaction (capture by EpCAM antibody), can only capture cancer cells expressing EpCAM, and the type of cancer cells that can be captured is limited.

CITATION LIST

Patent Literature

Patent Literature 1: JP 2005-523981 T

SUMMARY OF INVENTION

Technical Problem

The present invention aims to solve the problem and provide a method for capturing specific cells (e.g. many types of cancer cells, including cancer cells not expressing EpCAM), and a method for analysis of specific cells involving the method.

Solution to Problem

The present invention relates to a method for capturing specific cells present in blood or biological fluid, the method including: subjecting sampled blood or biological fluid to enrichment; and capturing specific cells therefrom onto a hydrophilic polymer layer in a flow field.

The specific cells are preferably cancer cells.

The enrichment is preferably carried out by centrifugation.

The sampled blood or biological fluid is preferably diluted before the enrichment.

Preferably, a buffer solution or a liquid medium is used for the dilution.

The flow field is preferably formed by shaking.

The hydrophilic polymer layer is preferably formed of at least one hydrophilic polymer selected from the group consisting of poly(meth)acryloylmorpholine and polymers represented by the following formula (I):

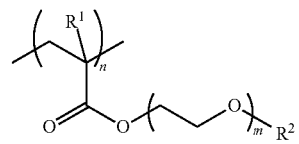

wherein $R^1$ represents a hydrogen atom or a methyl group, $R^2$ represents an alkyl group, m represents 1 to 5, and n represents the number of repetitions.

The hydrophilic polymer layer is preferably formed of a copolymer of at least one hydrophilic monomer selected from the group consisting of (meth)acryloylmorpholine and compounds represented by the following formula (I-1):

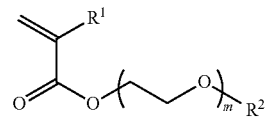

wherein $R^1$, $R^2$, and m are as defined above, with an additional monomer.

The hydrophilic polymer layer preferably has a thickness of 10 to 500 nm.

Another aspect of the present invention relates to a method for analysis of specific cells, including capturing specific cells from blood or biological fluid by the method for capturing specific cells, and analyzing the specific cells.

Advantageous Effects of Invention

The method for capturing specific cells present in blood or biological fluid according to the present invention includes subjecting sampled blood or biological fluid to enrichment, and capturing specific cells therefrom onto a hydrophilic polymer layer in a flow field. In particular, since the capturing step in this method is performed in a flow field, blood cells including red and white blood cells and platelets can be poorly captured, while specific cells such as cancer cells can be less affected by the flow field or, on the contrary, can be better captured. Hence, it is possible to effectively capture specific cells (e.g. many types of cancer cells, including cancer cells not expressing EpCAM) and thus to selectively capture the specific cells such as cancer cells.

BRIEF DESCRIPTION OF DRAWINGS

FIG. 1 shows exemplary schematic views of a multi-well plate having wells with a hydrophilic polymer layer formed thereon.

DESCRIPTION OF EMBODIMENTS

The method for capturing specific cells present in blood or biological fluid of the present invention includes subjecting sampled blood or biological fluid to enrichment, and capturing specific cells therefrom onto a hydrophilic polymer layer in a flow field.

Specifically, according to the present method, blood or biological fluid sampled from, e.g. the body may be first subjected to an enrichment treatment, e.g. via centrifugation, to prepare a sample having levels of blood cells and the like lower than the sampled blood or biological fluid. Then, the sample may be contacted with a hydrophilic polymer layer in a flow field to capture specific cells such as cancer cells from the sample. Thus, firstly, since the enrichment treatment reduces the cell adhesion-inhibiting effect of blood cells and the like, the treated specific cells exhibit their inherent ability to adhere to hydrophilic polymers. Additionally, since the capturing step is performed in the flow field, blood cells including red and white blood cells and platelets can be poorly captured, while specific cells such as cancer cells can be less affected by the flow field or, on the contrary, can be better captured, as compared with methods with no flow field. Therefore, the present method is effective in selectively capturing specific cells to an extent that could never be achieved without a flow field.

Thus, tumor cells and the like in blood or biological fluid can be effectively captured onto a hydrophilic polymer layer. Then, it can be expected that by counting the number of captured tumor cells and the like, one can determine the number of tumor cells and the like in the blood or biological fluid, e.g. in order to evaluate the cancer-treating effect. Moreover, the captured tumor cells and the like may be cultured and then used to determine the effect of drugs such as anticancer drugs. This allows us to determine the effect of drugs such as anticancer drugs ex vivo before administration, and also helps to screen drugs such as anticancer drugs.

Examples of specific cells that may be used in the method for capturing specific cells include cancer cells (any cancer cells, including cancer cells not expressing EpCAM). Examples of the cancer cells include circulating tumor cells (CTCs).

The method for capturing specific cells includes first subjecting sampled blood or biological fluid to enrichment. The enrichment treatment may be any treatment that enriches blood or biological fluid. In particular, it can be suitably carried out by centrifugation.

The centrifugation process is preferably performed at a centrifugal force of 200 to 3000 G (×g). A centrifugal force of 200 G or higher can provide improved separation of blood cells and reduction in the loss of specific cells (the loss due to the specific cells being incorporated into the fraction of red blood cells and the like), thereby being effective in selectively capturing specific cells. A centrifugal force of 3000 G or lower can result in reduced stress on specific cells, thereby maintaining their original nature. The centrifugal force is more preferably 300 to 2800 G, still more preferably 400 to 2500 G.

The duration and temperature of the centrifugation may be appropriately selected, e.g. in view of the ability to separate blood cells. For example, the centrifugation may be performed for 1 to 120 minutes, preferably 1 to 60 minutes, at 2 to 40° C., preferably 3 to 30° C. The centrifugation process may be carried out by known techniques, such as using a known centrifugal separator.

In the centrifugation process, the sampled blood or biological fluid may be centrifuged, followed by removing the supernatant containing platelets to prepare a sample having a platelet level lower than the sampled blood or biological fluid. Moreover, the sampled blood or biological fluid may be centrifuged, followed by separating an intermediate mononuclear cell layer to separate and remove red blood cells and platelets, thereby preparing a sample with an increased level of specific cells such as cancer cells.

The method for capturing specific cells may include, prior to the enrichment treatment, an additional treatment to reduce protein levels in the blood or biological fluid. The additional treatment to reduce protein levels in the blood or biological fluid may be carried out, for example, by diluting the sampled blood or biological fluid. The dilution may be performed using a buffer solution such as a phosphate buffered saline (PBS) having the same pH as human blood (about 7.4) or a liquid medium such as Dulbecco's modified eagle's medium (DMEM). Specifically, it may be carried out by diluting the sampled blood or biological fluid with a buffer solution, or adding the sampled blood or biological fluid to a liquid medium for dilution, to obtain protein levels lower than the sampled blood or biological fluid.

In the method for capturing specific cells, the enrichment treatment, optionally preceded by the additional treatment, is followed by capturing specific cells onto a hydrophilic polymer layer in a flow field.

The hydrophilic polymer layer (the layer formed of a hydrophilic polymer) may be formed on a certain substrate. Examples of the substrate include acrylic resins (polyacrylic resins) such as polymethyl acrylate, polymethyl methacrylate, polyacrylic acid, and polymethacrylic acid; cycloolefin resins (polycycloolefins); carbonate resins (polycarbonates); styrene resins (polystyrenes); polyester resins such as polyethylene terephthalate (PET); polydimethylsiloxanes; and glass such as soda-lime glass and borosilicate glass.

The hydrophilic polymer layer (the layer formed of a hydrophilic polymer) preferably has a thickness of 10 to 500 nm, more preferably 30 to 400 nm, still more preferably 50 to 350 nm. When the thickness is adjusted within the range indicated above, selective capture of cancer cells and low adsorption of other proteins and cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with an additional monomer. Examples of such homopolymers and copolymers include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomers may be any monomer containing a hydrophilic group. Examples of the hydrophilic group include known hydrophilic groups such as an amide group, a sulfuric acid group, a sulfonic acid group, a carboxylic acid group, a hydroxyl group, an amino group, and an oxyethylene group.

Specific examples of the hydrophilic monomers include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives containing cyclic groups (e.g., (meth)acryloylmorpholine). Preferred among these are (meth)acrylic acid, (meth)acrylic acid esters, alkoxyalkyl (meth) acrylates, and (meth) acryloylmorpholine, with alkoxyalkyl (meth) acrylates being more preferred, with 2-methoxyethyl acrylate being particularly preferred.

The additional monomer may be appropriately selected as long as it does not inhibit the effects of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and polymers represented by the following formula (I):

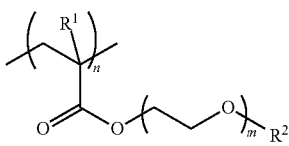

(I)

wherein $R^1$ represents a hydrogen atom or a methyl group, $R^2$ represents an alkyl group, m represents 1 to 5, and n represents the number of repetitions.

The alkyl group represented by $R^2$ preferably has 1 to 10 carbon atoms, more preferably 1 to 5 carbon atoms. In particular, $R^2$ is particularly preferably a methyl group or an ethyl group. The symbol m is preferably 1 to 3. The symbol n (number of repeating units) is preferably 15 to 1500, more preferably 40 to 1200.

Alternatively, the hydrophilic polymer may also suitably be a copolymer of at least one hydrophilic monomer selected from the group consisting of (meth) acryloylmorpholine and compounds represented by the formula (I-1) below with an additional monomer.

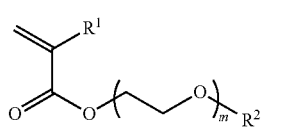

(I-1)

In formula (I-1), $R^1$, $R^2$, and m are as defined above.

The surface of the hydrophilic polymer layer preferably at least partially (partially or entirely) has a contact angle with water of 25 to 75°, more preferably 35 to 75°, still more preferably 35 to 70°. When the hydrophilic polymer layer has such a predetermined contact angle with water, the effects of the present invention can be well achieved.

The hydrophilic polymer layer may be formed by dissolving or dispersing a hydrophilic polymer in any solvent to prepare a hydrophilic polymer solution or dispersion, and entirely or partially coating the surface of a substrate with the hydrophilic polymer solution or dispersion by a known method, such as (1) by injecting the hydrophilic polymer solution or dispersion into the substrate surface (the recess of the substrate) and retaining and drying it for a predetermined time, or (2) by applying (spraying) the hydrophilic polymer solution or dispersion to the substrate surface and retaining and drying it for a predetermined time. Thus, a substrate provided with a polymer layer formed of a hydrophilic polymer can be prepared. Then, the substrate provided with a hydrophilic polymer layer may be combined with other components as needed, to prepare an apparatus capable of analyzing specific cells.

The solvent, injection method, application (spraying) method, and other conditions may be conventionally known materials or methods.

The retention/drying time in the method (1) or (2) may be selected appropriately according to the size of the substrate, the type of liquid introduced, and other factors. The retention time is preferably five minutes to ten hours, more preferably ten minutes to five hours, still more preferably 15 minutes to two hours. The drying is preferably performed at room temperature (about 23° C.) to 80° C., more preferably at room temperature to 50° C. Moreover, the drying may be carried out under reduced pressure. Furthermore, the hydrophilic polymer solution or dispersion may be retained for a certain period of time, optionally followed by discharging the excess solution or dispersion before drying.

The solvent may be any solvent that can dissolve the hydrophilic polymer and may be selected appropriately according to the hydrophilic polymer used. Examples include water, organic solvents, and solvent mixtures thereof. Examples of the organic solvents include alcohols such as methanol, ethanol, n-propanol, i-propanol, and methoxypropanol, ketones such as acetone and methyl ethyl ketone, tetrahydrofuran, acetonitrile, ethyl acetate, and toluene.

In the method for capturing specific cells, the sample (sample having lower blood cell levels) prepared by subjecting blood or biological fluid to an enrichment treatment may be contacted with the substrate provided with a hydrophilic polymer layer in a flow field to capture specific cells.

The term "flow field" used in the method for capturing specific cells means conditions where the sample is flowing (moving). In the present invention, the capture onto the hydrophilic polymer layer is performed while the sample is flowing. The flow field may suitably be formed by, for example, shaking.

The shaking may be carried out in any manner, preferably, for example, by reciprocal shaking, rotary shaking, figure-of-eight shaking, wave shaking, or seesaw shaking, and more preferably by wave shaking. Such shaking may be produced by known shakers.

The shaking speed (the number of rotations of the shaker) is preferably 1 to 100 rpm, more preferably 5 to 50 rpm, still more preferably 10 to 30 rpm. The tilt angle during the shaking (shaking angle) is preferably 1 to 40 degrees, more preferably 2 to 20 degrees, still more preferably 3 to 10 degrees. The temperature and duration of the shaking may be appropriately selected, e.g. in view of the ability to capture specific cells. For example, the shaking may be performed at room temperature (about 23° C.) to 45° C. for 1 to 360 minutes.

Contacting the sample with the hydrophilic polymer layer may be carried out by any method capable of this contact, such as by injecting or applying (spraying) the sample.

By contacting the sample with the hydrophilic polymer layer in the flow field, the specific cells present in the sample can be captured onto the hydrophilic polymer layer while reducing adsorption of blood cells and the like. Thus, the specific cells may be selectively captured onto the hydrophilic polymer layer, for example, by retaining the contacted sample in the flow field for a predetermined time and then washing it. Then, it can be expected that by counting the number of captured specific cells, one can determine the number of specific cells in the sampled blood or biological fluid, e.g. in order to evaluate the cancer-treating effect.

The method for capturing specific cells may be performed using, for example, a device that includes a substrate such as a multi-well plate or a chamber slide, optionally with additional components. FIG. 1 illustrates an exemplary multi-well plate 1.

The multi-well plate 1 in FIG. 1 is a device intended to capture specific cells in which wells 11 are arranged in so-called matrix form. The multi-well plate 1 has multiple wells 11 having a circular opening. The wells 11 are recesses into which a sample may be injected that is prepared by subjecting sampled blood or biological fluid to an enrichment treatment to reduce the levels of blood cells and the like. Specific cells can be effectively captured when the sample injected in a flow field is subjected to analysis as compared to when the sampled blood or biological fluid is directly subjected to analysis. Thus, it is possible to confirm the presence or absence of specific cells in blood or biological fluid, count the number of specific cells, culture the specific cells, determine the effect of drugs, and screen the drugs.

Although FIG. 1 illustrates a 24-well plate having 24 wells 11 arranged in 4 rows by 6 columns as an example, it is sufficient for the multi-well plate 1 to have at least two wells 11, and any number of wells 11 may be provided. Examples other than the 24-well plate include general multi-well plates in which the number of wells 11 is 6, 96, 384, etc.

Each well 11 is a non-through hole which is opened at the surface of the multi-well plate 1. A sample prepared by subjecting blood or biological fluid to an enrichment treatment may be injected into the wells 11 through the respective openings. If the presence of specific cells is confirmed, a culture fluid for culturing the specific cells may also be injected.

The diameter R of the opening and the depth D of each well 11 are not particularly critical, and may be those of a conventional multi-well plate 1. Although in FIG. 1, the inner side surface of each well 11 is substantially vertical to the opposite faces of the multi-well plate 1, the inner side surface of the wells 11 may be inclined to taper from the opening to the bottom. Alternatively, the inner side surface may be inclined to flare out from the opening to the bottom.

Though the wells 11 in FIG. 1 are circularly opened, the openings of the wells 11 may be of any shape such as quadrangle.

The multi-well plate 1 may suitably be one in which the multiple wells 11 are separable. When multiple wells are provided, they may be separated into wells for counting the number of specific cells and for culturing the specific cells. For example, the presence or absence of specific cells may first be confirmed in the wells for counting, and if the presence is confirmed, the specific cells may then be cultured in the wells for culturing and then used to determine the effect of drugs. In a suitable chamber slide, the number of chambers is at least one but not more than ten.

In the multi-well plate 1 or chamber slide, the wells 11 preferably have a hydrophilic polymer layer formed at least partially on the inner surface thereof. In the example shown in FIG. 1, a hydrophilic polymer layer 21 is formed on the bottom surface and a part of the side surface of the wells 11.

Once a sample prepared by subjecting blood or biological fluid to an enrichment treatment is introduced into the wells 11 and shaken using a shaker (flow field), the specific cells present in the sample can be captured onto the hydrophilic polymer layer 21 while reducing adsorption of blood cells and the like. Thus, the specific cells may be selectively captured onto the hydrophilic polymer layer 21 by retaining the introduced sample in a flow field for a predetermined time and then washing it.

The method for analysis of specific cells according to the present invention includes capturing specific cells such as cancer cells from blood or biological fluid by the method described above, and analyzing the specific cells. This method can capture specific cells (e.g. many types of cancer cells, including cancer cells not expressing EpCAM). Moreover, this method can sufficiently capture specific cells from blood or biological fluid while reducing adhesion or attachment of other proteins and cells, thereby selectively capturing the specific cells.

In the method for analysis of specific cells, the hydrophilic polymer layer may suitably be contacted with blood from which blood cells and the like have been removed. This can further enhance selective capture of specific cells such as cancer cells. The removal of blood cells and the like may be carried out by known techniques, such as membrane separation as well as centrifugation as described above.

EXAMPLES

The present invention is specifically described with reference to, but not limited to, examples below.

Device Example 1

Using azobisisobutyronitrile (AIBN), 2-methoxyethyl acrylate was thermally polymerized at 80° C. for six hours to produce poly(2-methoxyethyl acrylate) (molecular weight: Mn=about 15,000, Mw=about 50,000). Then, a 1.0% by mass solution of the poly(2-methoxyethyl acrylate) in methanol was prepared.

The poly(2-methoxyethyl acrylate) solution (1% by mass) was injected into the wells of a polystyrene 24-well plate and left for 30 minutes at room temperature. Thereafter, the solution was partly drawn using a pipette, followed by drying to prepare a medical analysis device.

Device Example 2

A medical analysis device was prepared as in Device Example 1, except that the concentration of the poly(2-methoxyethyl acrylate) solution was changed to 2.5% by mass.

Device Example 3

A medical analysis device was prepared as in Device Example 1, except that the concentration of the poly(2-methoxyethyl acrylate) solution was changed to 5.0% by mass.

Device Example 4

A medical analysis device was prepared as in Device Example 1, except that a borosilicate glass chamber slide was used, and the concentration of the poly(2-methoxyethyl acrylate) solution was changed to 0.3% by mass.

Device Example 5

A medical analysis device was prepared as in Device Example 4, except that the concentration of the poly(2-methoxyethyl acrylate) solution was changed to 0.5% by mass.

Device Example 6

A medical analysis device was prepared as in Device Example 1, except that no poly(2-methoxyethyl acrylate) solution was injected and no poly(2-methoxyethyl acrylate) layer was formed.

[Thickness of Hydrophilic Polymer Layer (Coating Layer)]

The thickness of the hydrophilic polymer layer of the medical analysis devices was determined by measuring (photographing) a cross section of the hydrophilic polymer layer using a TEM at an accelerating voltage of 15 kV and a magnification of 1000 times.

[Contact Angle with Water]

A volume of 2 μL of distilled water was dropped onto the surface of the hydrophilic polymer layer of each medical analysis device. Thirty seconds later, the contact angle was measured by the θ/2 method at room temperature.

[Analysis of Whole Blood Spiked with Cancer Cells]

Stained human colon adenocarcinoma (HT-29) cells were suspended in whole blood to a concentration of 100 cells per mL of blood to prepare spiked blood. The spiked blood was diluted with an equal volume of a liquid medium to prepare a spiked blood dilution. Next, to a 15 ml centrifuge tube were added a solution for isolation (Lymphoprep, density=1.077±0.001 g/mL) and then the spiked blood dilution, followed by centrifugation at 800 G for 20 minutes at room temperature (about 23° C.). Then, the mononuclear cell layer was separated. To the separated mononuclear cell layer was added a phosphate buffer (PBS) solution, followed by centrifugation again to enrich the mononuclear cell layer. After the centrifugation, the aggregates at the lowermost layer were suspended in a liquid medium containing 10% fetal bovine serum (FBS) in a volume equal to the initial whole blood volume. A 1 ml portion of the suspension was injected into each well or chamber and left at 37° C. for one hour to cause adhesion under static conditions (without shaking) or under shaking. Then, non-adhered cells were washed away with a PBS solution. Thereafter, the number of adhered cancer cells was counted using a fluorescence microscope.

The shaking was carried out by wave shaking (tilt angle 6°, 20 rpm) at 37° C. using a Wave-PR shaker available from Taitec Corporation.

TABLE 1

|  | Device Example 1 | | Device Example 2 | | Device Example 3 | |
| --- | --- | --- | --- | --- | --- | --- |
|  | Example 1 | Comparative Example 1 | Example 2 | Comparative Example 2 | Example 3 | Comparative Example 3 |
| Shaking | Performed | Not performed | Performed | Not performed | Performed | Not performed |
| Thickness of hydrophilic polymer layer (coating layer) (nm) | 39 | 39 | 86 | 86 | 280 | 280 |
| Contact angle with water (°) | 43 | 43 | 50 | 50 | 60 | 60 |
| Analysis of whole blood spiked with cancer cells (number of cells) | 62 | 48 | 69 | 55 | 78 | 58 |

|  | Device Example 4 | | Device Example 5 | | Device Example 6 | |
| --- | --- | --- | --- | --- | --- | --- |
|  | Example 4 | Comparative Example 4 | Example 5 | Comparative Example 5 | Comparative Example 6 | Comparative Example 7 |
| Shaking | Performed | Not performed | Performed | Not performed | Performed | Not performed |
| Thickness of hydrophilic polymer layer (coating layer) (nm) | 108 | 108 | 450 | 450 | 0 | 0 |
| Contact angle with water (°) | 52 | 52 | 65 | 65 | 85 | 85 |
| Analysis of whole blood spiked with cancer cells (number of cells) | 60 | 45 | 68 | 48 | 43 | 47 |

When a sample prepared by subjecting blood or biological fluid to an enrichment treatment was contacted with a hydrophilic polymer layer (coating layer) in a flow field, specific cells such as cancer cells were selectively captured, and the number of adhered specific cells was increased.

REFERENCE SIGNS LIST 1 multi-well plate
11 well
21 hydrophilic polymer layer

The invention claimed is:

1. A method for capturing cancer cells present in blood or biological fluid, the method comprising:

subjecting sampled blood or biological fluid to enrichment; and capturing cancer cells from the enriched blood or biological fluid on a hydrophilic polymer layer in a flow field, wherein the flow field is formed by shaking, the shaking speed is 5 to 50 rpm, and a tilt angle is 2 to 20 degrees.

2. The method for capturing cancer cells according to claim 1, wherein the enrichment is carried out by centrifugation.

3. The method for capturing cancer cells according to claim 1, wherein the sampled blood or biological fluid is diluted before the enrichment.

4. The method for capturing cancer cells according to claim 3, wherein a buffer solution or a liquid medium is used for the dilution.

5. The method for capturing cancer cells according to claim 1, wherein the hydrophilic polymer layer is formed of at least one hydrophilic polymer selected from the group consisting of poly(meth)acryloylmorpholine and polymers represented by the following formula (I):

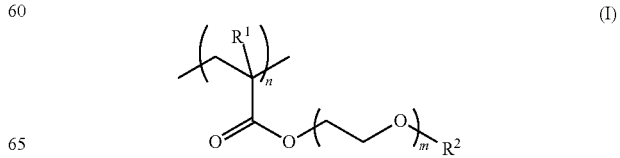

wherein R¹ represents a hydrogen atom or a methyl group, R² represents an alkyl group, m represents 1 to 5, and n represents the number of repetitions.

6. The method for capturing cancer cells according to claim 1,
wherein the hydrophilic polymer layer is formed of a copolymer of at least one hydrophilic monomer selected from the group consisting of (meth)acryloylmorpholine and compounds represented by the following formula (I-1):

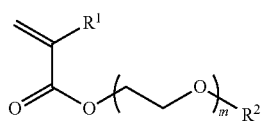
(I-1)

wherein R¹ represents a hydrogen atom or a methyl group, R² represents an alkyl group, and m represents 1 to 5, with an additional monomer.

7. The method for capturing cancer cells according to claim 1, wherein the hydrophilic polymer layer has a thickness of 10 to 500 nm.

8. A method for analysis of specific cells, comprising capturing cells from blood or biological fluid by the method for capturing cells according to claim 1, and analyzing the specific cells.

9. The method for capturing cancer cells according to claim 1, wherein the shaking is performed at about 23° C. to 45° C. for 1 to 360 minutes.

10. The method for capturing cancer cells according to claim 1, wherein the shaking is carried out in wave shaking.

* * * * *